US00PP35121P2

(12) United States Plant Patent
Woolmore

(10) Patent No.: US PP35,121 P2
(45) Date of Patent: Apr. 25, 2023

(54) ***PHORMIUM* PLANT NAMED 'PKFJTB18'**

(50) Latin Name: *Phormium tenax*
Varietal Denomination: PKFJTB18

(71) Applicant: Malcolm Peter Woolmore, Auckland (NZ)

(72) Inventor: Malcolm Peter Woolmore, Auckland (NZ)

(73) Assignee: KiwiFlora Ltd., Auckland (NL)

( * ) Notice: Subject to any disclaimer, the term of this patent is extended or adjusted under 35 U.S.C. 154(b) by 0 days.

(21) Appl. No.: 17/803,536

(22) Filed: Aug. 15, 2022

(51) Int. Cl.
*A01H 5/00* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./373, 226
CPC ..... A01H 5/00
See application file for complete search history.

(56) References Cited

PUBLICATIONS https://cascadiannurseries.com/wp-content/uploads/2022/04/2022-Featured-Plants.pdf; 2022; 2 pages.*
https://twitter.com/MonroviaPlants/status/1523707380361482240; May 9, 2022; 1 page.*

* cited by examiner

*Primary Examiner* — Kent L Bell

(57) ABSTRACT

A new cultivar of *Phormium* plant named 'PKFJTB18' that is characterized by a moderate overall size, young leaves that are variegated with a grey-brown center band, pink stripes on both sides of the center band and red-orange margins, young leaves that are upright and mature leaves that are outwardly arching, a basal clump that is yellow-green in color and a good multiplication rate by division.

1 Drawing Sheet

Botanical classification: *Phormium tenax.*
Variety denomination: 'PKFJTB18'.

BACKGROUND OF THE INVENTION

The present invention relates to a new and distinct cultivar of *Phormium* plant botanically known as *Phormium tenax* and hereinafter referred to by the cultivar name 'PKFJTB18'.

'PKFJTB18' was discovered as a naturally occurring whole plant mutation within a commercial crop of *Phormium tenax* 'Sundowner' (not patented) in 2009. The new cultivar was discovered as a single plant in a cultivated area of Whenuapai, Auckland, New Zealand. The new cultivar was discovered in a commercial plant nursery container field.

Asexual reproduction of the new cultivar 'PKFJTB18' first occurred by division in 2010 in Whenuapai, Auckland, New Zealand. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Phormium* cultivar 'PKFJTB18'. These traits in combination distinguish 'PKFJTB18' as a new and distinct cultivar apart from other existing varieties of *Phormium* known by the inventor.

1. *Phormium* 'PKFJTB18' exhibits a moderate overall size.

2. *Phormium* 'PKFJTB18' exhibits young leaves that are variegated with a grey-brown center band, pink stripes on both sides of the center band and red-orange margins.
3. *Phormium* 'PKFJTB18' exhibits young leaves that are upright and mature leaves that are outwardly arching.
4. *Phormium* 'PKFJTB18' exhibits a basal clump that is yellow-green in color.
5. *Phormium* 'PKFJTB18' exhibits a good multiplication rate by division.

The closest comparison cultivars are *Phormium* 'Evening Glow' (not patented) and *Phormium* 'Rainbow Sunrise' (not patented). 'PKFJTB18' is distinguishable from 'Evening Glow' by the following characteristics:

1. *Phormium* 'PKFJTB18' exhibits a moderate overall size. In comparison, 'Evening Glow' has a larger overall size than the overall size of 'PKFJTB18'.
2. *Phormium* 'PKFJTB18' exhibits young leaves that are variegated with a grey-brown center band, pink stripes on both sides of the center band and red-orange margins. In comparison, the leaves of 'Evening Glow' are red-pink with darker red-purple margins.
3. *Phormium* 'PKFJTB18' exhibits young leaves that are upright and mature leaves that are outwardly arching. In comparison, both young and mature leaves of 'Evening Glow' are outwardly arching.
4. *Phormium* 'PKFJTB18' exhibits leaves that are wider than the leaves of 'Evening Glow'. The leaves of 'PKFJTB18' average 45 mm. in width while the leaves of 'Evening Glow' average 35 mm. in width.

'PKFJTB18' is distinguishable from 'Rainbow Sunrise' by the following characteristics:

1. *Phormium* 'PKFJTB18' exhibits a moderate overall size. In comparison, 'Rainbow Sunrise' has a larger overall size than the overall size of 'PKFJTB18'.
2. *Phormium* 'PKFJTB18' exhibits young leaves that are variegated with a grey-brown center band, pink stripes on both sides of the center band and red-orange margins. In comparison, the leaves of 'Rainbow Sunrise' are rose-pink and fade to pale yellow with bronze-green margins.
3. *Phormium* 'PKFJTB18' exhibits young leaves that are upright and mature leaves that are outwardly arching. In comparison, both young and mature leaves of 'Rainbow Sunrise' are upright.
4. *Phormium* 'PKFJTB18' exhibits leaves that are wider than the leaves of 'Rainbow Sunrise'. The leaves of 'PKFJTB18' average 45 mm. in width while the leaves of 'Rainbow Sunrise' average 35 mm. in width.

'PKFJTB18' is distinguishable from the parent plant *Phormium* 'Sundowner' by the following characteristics:

1. *Phormium* 'PKFJTB18' exhibits a moderate overall size. In comparison, 'Sundowner' has a larger overall size than the overall size of 'PKFJTB18'.
2. *Phormium* 'PKFJTB18' exhibits young leaves that are variegated with a grey-brown center band, pink stripes on both sides of the center band and red-orange margins. In comparison, the leaves of 'Sundowner' are bronze-green with rose-pink margins fading to cream color.
3. *Phormium* 'PKFJTB18' exhibits young leaves that are upright and mature leaves that are outwardly arching. In comparison, both young and mature leaves of 'Sundowner' are upright.
4. *Phormium* 'PKFJTB18' exhibits leaves that are narrower than the leaves of 'Sundowner'. The leaves of 'PKFJTB18' average 45 mm. in width while the leaves of 'Sundowner' average 75 mm. in width.

BRIEF DESCRIPTION OF THE DRAWING

The accompanying photograph illustrates the distinguishing traits of *Phormium* 'PKFJTB18'. The photograph shows an overall view of a 3 year old plant. The photograph was taken using conventional techniques and although colors may appear different from actual colors due to light reflectance, it is as accurate as possible by conventional photographic techniques. The colors in the photograph may differ slightly from the color values cited in the detailed botanical description, which accurately describe the colors of the new *Phormium*.

BOTANICAL DESCRIPTION OF THE PLANT

The following is a detailed description of the new *Phormium* cultivar named 'PKFJTB18'. Data was collected in Auckland, New Zealand from 3 year old plants grown in 25 liter containers under an open sided 60 percent shade cover. The time of year was autumn in the southern hemisphere and the average temperature was 15.5 degrees Centigrade during the day and 14 degrees Centigrade at night. Color determinations are in accordance with The Royal Horticultural Society Colour Chart 2015 edition, except where general color terms of ordinary dictionary significance are used. The growing requirements are similar to the species. 'PKFJTB18' has not been tested under all possible conditions and phenotypic differences may be observed with variations in environmental, climatic, and cultural conditions, however, without any variance in genotype.

Botanical classification: *Phormium tenax* 'PKFJTB18'.

Parentage: *Phormium* 'PTKFJTB18' is a naturally occurring whole plant mutation of *Phormium* 'Sundowner'.

Annual or perennial: Perennial.

Plant type: Shrub.

Growth habit: Clump forming with basal shoots of lanceolate shaped leaves.

Plant shape: Rounded.

Suitable container size: 2 liter pots.

Plant height to top of foliage: Average 68 cm.

Plant width: Average 90 cm.

Vigor: Moderate.

Growth rate: Moderate.

Low temperature tolerance: −12° Centigrade.

High temperature tolerance: 35° Centigrade.

Propagation: Division.

Crop time: Approximately 12 months.

Root system: Fibrous older roots with fleshy young roots.

Plant fragrance: None.

Stem: Basal clump, acaulescent, color varies from 149D to 150D.

Foliage:

*Leaf arrangement.*—Leaves arise from basal clump.

*Compound or single.*—Single.

*Quantity of leaves per plant.*—Average 80.

*Leaf shape.*—Lanceolate.

*Leaf apex.*—Acuminate.

*Leaf base.*—Sheathed.

*Leaf orientation.*—Young leaves upright, mature leaves outwardly arching.

*Leaf dimensions.*—Average 65 cm. in length and 45 mm. in width.

*Leaf texture.*—Smooth (both surfaces).

*Leaf luster.*—Glossy (both surfaces).

*Pubescence.*—Absent (both surfaces).

*Leaf margin.*—Entire.

*Venation pattern.*—Parallel.

*Young leaf color* (*upper surface*).—N199A center band with stripes varying from 36A to 37C and margins N34B.

*Young leaf color* (*lower surface*).—N197A center band with stripes 37B and margins N34B.

*Mature leaf color* (*upper surface*).—199A center band with stripes 18B and margins 168B.

*Mature leaf color* (*lower surface*).—199D center band with stripes 18B and margins 168B.

*Durability of foliage to stress.*—High.

Flower: 'PKFJTB18' has not produced flowers to date.

Fruit and seed: 'PKFJTB18' has not produced fruit or seed to date.

Other plant characteristics: Dry tolerant, coastal climate tolerant, foliage exhibits good wind and rain resistance.

Disease and pest resistance: Disease and pest resistance do not differ from other *Phormium* varieties.

The invention claimed is:

1. A new and distinct variety of *Phormium* plant named 'PKFJTB18' as described and illustrated.

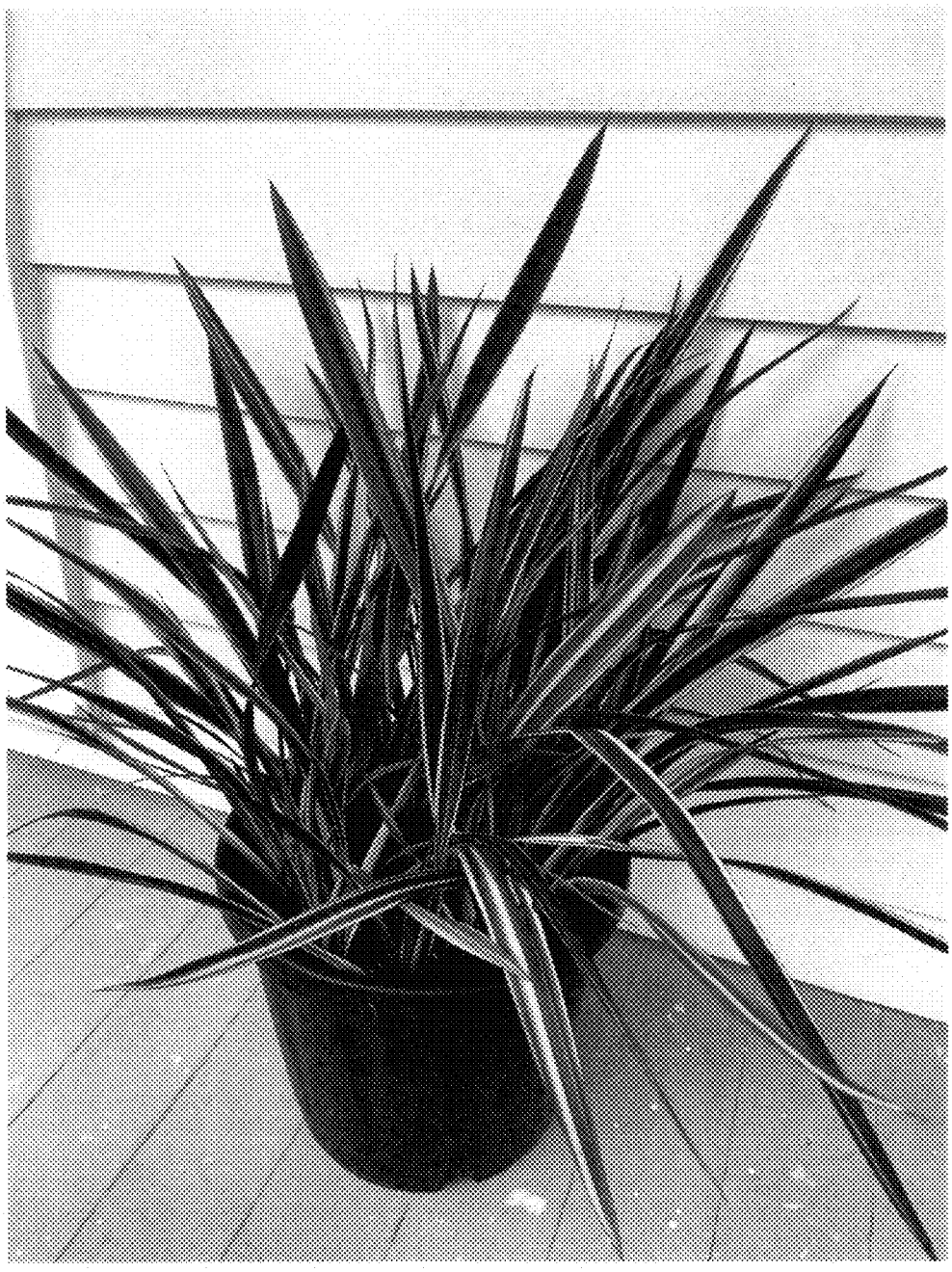

* * * * *